United States Patent
Couvillon, Jr.

(10) Patent No.: US 7,303,528 B2
(45) Date of Patent: Dec. 4, 2007

(54) SERIALIZATION OF SINGLE USE ENDOSCOPES

(75) Inventor: Lucien Alfred Couvillon, Jr., Concord, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 449 days.

(21) Appl. No.: 10/848,730

(22) Filed: May 18, 2004

(65) Prior Publication Data

US 2005/0261551 A1 Nov. 24, 2005

(51) Int. Cl.
*A61B 1/04* (2006.01)
*H04N 7/18* (2006.01)

(52) U.S. Cl. .................. 600/118; 600/109; 348/74
(58) Field of Classification Search .............. 600/117, 600/118, 109; 348/72, 74
See application file for complete search history.

(56) References Cited

U.S. PATENT DOCUMENTS

| | | | |
|---|---|---|---|
| 4,897,789 A | 1/1990 | King et al. | |
| 4,996,975 A | 3/1991 | Nakamura | |
| 5,820,547 A | 10/1998 | Strobl et al. | |
| 5,830,121 A * | 11/1998 | Enomoto et al. | 600/117 |
| 5,871,439 A | 2/1999 | Takahashi et al. | |
| 6,313,868 B1 * | 11/2001 | D'Alfonso et al. | 348/72 |
| 6,511,418 B2 | 1/2003 | Shahidi et al. | |
| 6,517,478 B2 | 2/2003 | Khadem | |
| 6,651,669 B1 | 11/2003 | Burnside | |
| 7,033,316 B2 * | 4/2006 | Takahashi | 600/118 |
| 2001/0041825 A1 * | 11/2001 | Shibata et al. | 600/118 |
| 2002/0114452 A1 | 8/2002 | Hamilton | |
| 2002/0120179 A1 * | 8/2002 | Abe | 600/118 |
| 2003/0009083 A1 | 1/2003 | Takahashi | |
| 2003/0142205 A1 * | 7/2003 | Takahashi et al. | 348/65 |
| 2004/0082834 A1 * | 4/2004 | Onishi et al. | 600/118 |

FOREIGN PATENT DOCUMENTS

DE 20213926 U1 12/2002
JP 10 33472 A 2/1998

* cited by examiner

*Primary Examiner*—John P. Leubecker
(74) *Attorney, Agent, or Firm*—Klarquist Sparkman, LLP

(57) ABSTRACT

A system, device and method for serializing and authorizing a single use imaging device are provided. In one embodiment, the invention provides a single use imaging device comprising a memory having a stored code that includes a unique serial identifier. In another embodiment, the invention provides a system for authorizing a single use imaging device comprising a single use imaging device with an image of a verification object that includes a serial identifier uniquely associated with the device, a control unit capable of electronically receiving the verification object image, a decoder capable of extracting a serial identifier from the verification object image, a database of authorized serial identifiers, and means for determining if the single use imaging device is authorized.

27 Claims, 9 Drawing Sheets

SERIALIZATION OF SINGLE USE ENDOSCOPES

FIELD OF THE INVENTION

The present invention relates to serialization of medical devices in general and single use imaging devices in particular.

BACKGROUND OF THE INVENTION

As an aid to the early detection of disease, it has become well established that there are major public health benefits from regular endoscopic examinations of internal structures such as the alimentary canals and airways, e.g., the esophagus, lungs, colon, uterus, and other organ systems. A conventional imaging endoscope used for such procedures comprises a flexible tube with a fiber optic light guide that directs illuminating light from an external light source to the distal tip where it exits the endoscope and illuminates the tissue to be examined. An objective lens and fiber optic imaging light guide communicating with a camera at the proximal end of the scope, or an imaging camera chip at the distal tip, produce an image that is displayed to the examiner.

Navigation of the endoscope through complex and tortuous paths is critical to success of the examination with minimum pain, side effects, risk or sedation to the patient. To this end, modern endoscopes include means for deflecting the distal tip of the scope to follow the pathway of the structure under examination, with minimum deflection or friction force upon the surrounding tissue. Control cables similar to puppet strings are carried within the endoscope body in order to connect a flexible portion of the distal end to a set of control knobs at the proximal endoscope handle. By manipulating the control knobs, the examiner is able to steer the endoscope during insertion and direct it to a region of interest.

Conventional endoscopes are expensive medical devices costing in the range of $25,000 for an endoscope, and much more for the associated operator console. Because of the expense, these endoscopes are built to withstand repeated disinfections and use upon many patients. Conventional endoscopes are generally built of sturdy materials, which decreases the flexibility of the scope and thus can decrease patient comfort. Furthermore, conventional endoscopes are complex and fragile instruments that frequently need expensive repair as a result of damage during use or during a disinfection procedure.

Single use disposable medical devices have become popular for instruments with small lumens and intricate, delicate working mechanisms that are difficult to sterilize or clean properly. Single use disposable devices packaged in sterile wrappers avoid the risk of pathogenic cross-contamination of diseases such as HIV, hepatitis, and other pathogens. Hospitals generally welcome the convenience of single use disposable products because they no longer have to be concerned with product age, overuse, breakage, malfunction and sterilization. However, with the advent of single use devices comes the need for authorization of a particular device prior to use to determine if it is new or used, that associated console software is up-to-date (e.g., sensitivity and color calibration tables, steering algorithms, etc.), when and where it was manufactured, whether it is a current model, and information regarding recall notices. Therefore, in order to prevent improper use of single use devices, there is a need for a method of serializing a device so that prior to use, the user can be assured that the system is current, all elements are compatible, and the device can be authorized as new and unused, and ready for use.

SUMMARY OF THE INVENTION

To address these and other problems in the prior art, the present invention provides devices, systems and methods for serializing and authorizing a single use medical imaging device. The device form of the invention includes a single use imaging device having a shaft with a proximal and distal end and a connector on the proximal end for connecting the device to a control unit. An image sensor is included at or adjacent to the distal end for producing images in a predefined format for receipt by an imaging board within the control unit. The device includes a memory with a stored code encoding a serial identifier transferable to the control unit for analysis, wherein the serial identifier is uniquely associated with the imaging device at the time of manufacture. A transmit circuit is included that transmits the code to the imaging board in the format of the image signals produced by the image sensor.

In accordance with further aspects of the invention, another device form of the invention includes a control unit for authorizing a single use medical imaging device. The control unit comprises a connector for connecting the control unit to the single use medical imaging device and a device interface capable of receiving a code in a format of an image signal produced by an image sensor of the medical imaging device, wherein the code encodes a serial identifier uniquely associated with the single use imaging device. The control unit includes a processor that extracts the serial identifier from the code, and means for determining if the single use device is authorized based upon the serial identifier associated with the device. In some embodiments, the processor further includes logic for calibrating the single use imaging device upon authorization. In some embodiments, calibration includes imaging properties and also the navigation characteristics such as deflection ranges and sensitivities, dynamic and static, of the single use device. In further embodiments, the memory comprises logic for functionally testing the single use imaging device upon successful calibration.

In another aspect, the present invention provides a medical imaging system comprising a single use medical imaging device having an image of a verification object encoding a serial identifier uniquely associated with the device and a control unit for authorizing a single use medical imaging device. The control unit has a device interface capable of receiving the image of the verification object and means for determining if the single use device is authorized based upon the serial identifier encoded in the image. In some embodiments, the verification object image is stored in the memory of the single use device. In other embodiments, the verification object image is printed on a test target associated with the single use device. In some embodiments, the device is authorized by reference to a registry contained in a remote database accessible from the control unit via a network connection.

In another aspect, the present invention provides methods for authorizing a single use imaging device. The methods of this aspect of the invention comprise connecting the imaging device to a control unit, electronically obtaining an image of a prerecorded verification object associated with the imaging device, wherein the verification object encodes a serial identifier, extracting the serial identifier from the image, and authorizing the imaging device by comparing the serial identifier to a database containing information on authorized serial identifiers. A match between the serial identifier and information in the database results in the device being authorized for use. In some embodiments, the comparison is made to a remote database by connecting to a remote server. In some embodiments, the authentication method further comprises automatic calibration and functional self-testing.

In another aspect, the present invention provides methods for serializing a set of single use imaging devices comprising assigning a unique serial identifier to each device to be manufactured, encoding the serial identifier in a verification object image, wherein the verification object image also includes a set of calibration objects, associating the verification object with each imaging device at the time of its manufacture, and maintaining a registry of authorized serial identifiers corresponding to manufactured serialized imaging devices, wherein a user of an imaging device may determine if the device is authorized by comparing the serial identifier to the registry.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
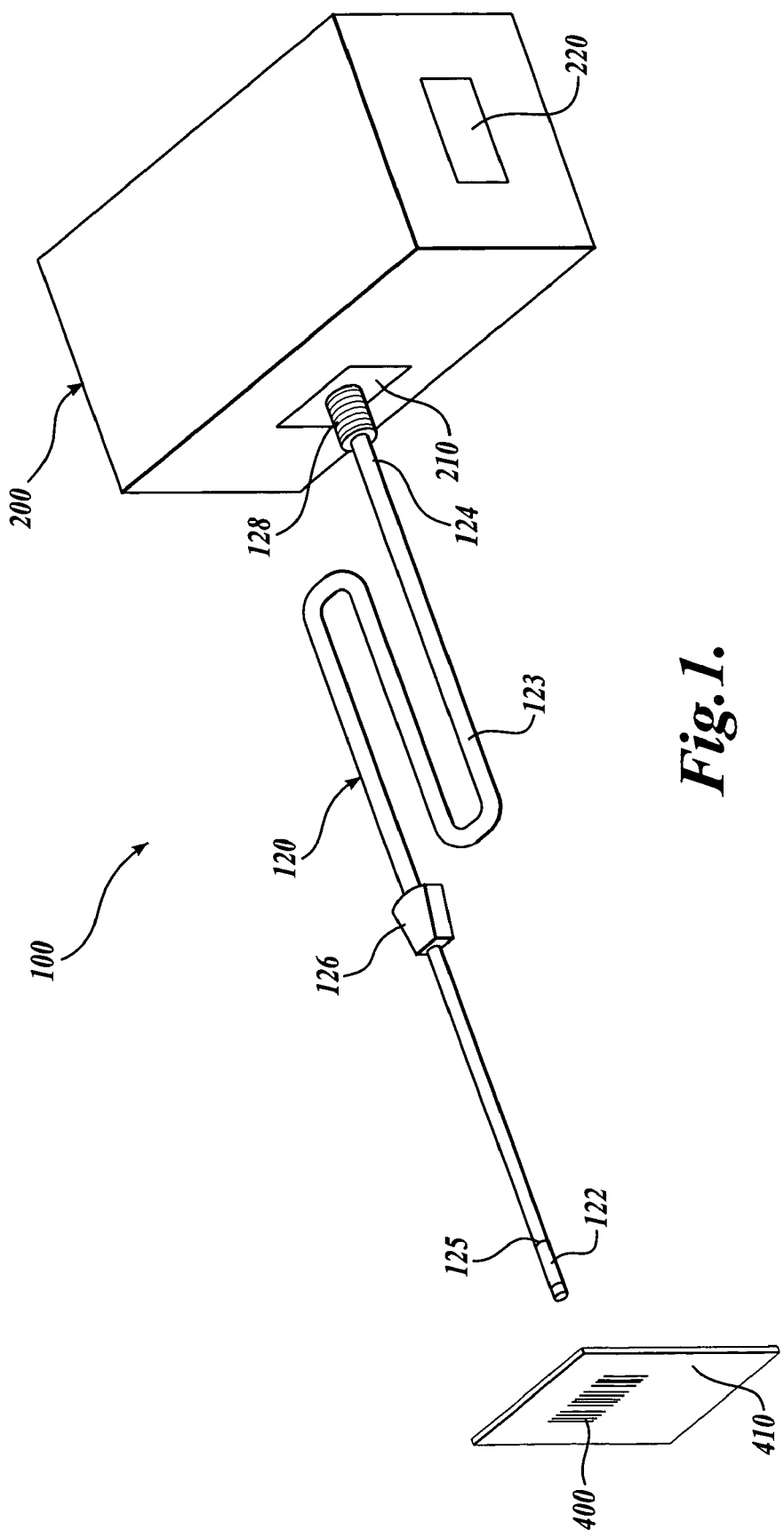
FIG. 1 is a schematic diagram illustrative of a system for authorizing a single use imaging device in accordance with an embodiment of the present invention.

Unless specifically defined herein, all terms used herein have the same meaning as they would be understood by those of ordinary skill in the art of the present invention. The following definitions are provided in order to provide clarity with respect to the terms as they are used in the specification and claims to describe the present invention.

As used herein, the term "verification object image" refers to any machine-readable image or portion thereof that is capable of encoding a serial identifier that is uniquely associated with a particular single use imaging device. A verification object image may include an encoded serial identifier and a set of imaging calibration objects. As used herein, the term "serial identifier" refers to any combination or arrangement of numbers, letters, symbols, characters, colors or patterns capable of uniquely identifying a single use imaging device. Typically, a serial identifier comprises at least 10 characters and may be many more, including possibly an Internet web address or URL. Examples of verification object images capable of encoding serial identifiers used in accordance with the devices, systems and methods of the invention include linear bar codes and two-dimensional bar codes as further described below.

Generally described, the present invention provides a system, device, and method for authorizing a single use imaging device prior to use. Single use imaging devices, such as endoscopes, imaging catheters, fiber optic guide wires and the like are useful to avoid the need to sterilize and repair complex and fragile instruments that frequently need expensive repair as a result of damage during use or during a disinfection procedure. The devices, systems and methods of the invention may be used to authorize single use imaging devices through the use of a unique serial identifier that is encoded in a verification object image that is associated with a single use device at the time of manufacture. In some embodiments, the code encoding the serial identifier is stored in the memory of the single use device. In other embodiments, the serial identifier is encoded in a verification object image that is printed on a test target that is associated with the single use device at the time of manufacture. In numerous embodiments, a remote central server authorizes the device. In further embodiments, the verification object is an image that includes an encoded serial identifier and a set of imaging calibration objects.

The various embodiments of the devices, systems and methods of the present invention may be used by any user who would benefit from devices, systems and methods for authenticating an imaging device, such as, for example, manufacturers and retailers of medical devices, physicians, surgeons, and other medical personnel, as well as patients. For example, the devices, systems and methods of the invention may be used to verify that a single use medical device is new and unused, of current production, and to further update operation parameters as well as to obtain recall information from a remote central registry.

The detailed description is divided into six sections. In the first section, a brief introductory overview of the system for authorizing a single use imaging device is provided. In the second section, a device in the form of a single use imaging device comprising a memory with a stored code encoding a serial identifier is presented. In the third section, a device in the form of a control unit that interfaces with a single use imaging device in accordance with one embodiment of the invention is presented. In the fourth section, a medical imaging system comprising a single use imaging device with a verification object image is provided. In the fifth section, a method for authorizing a single use imaging device is presented. Finally, in the sixth section, a method of serializing single use imaging devices is described.

For ease of understanding, a brief overview of certain aspects of the exemplary authorization system 100 for a single use imaging device is illustrated by FIG. 1. The authorization system 100 includes a verification object image 400 that is printed on a test target 410. A single use imaging device 120, such as an endoscope, comprises a shaft 123 having a distal tip 122 that includes an imaging element and a proximal end 124 with a connector 128 that is attachable to a control unit 200. Proximal to the distal tip 122 is an articulation joint 125 that provides sufficient flexibility to the distal section of the shaft such that the distal tip 122 can be directed over the required deflection range (180° or more) by the steering mechanism and can be directed to make that bend in any direction desired about the circumference of the distal tip. In the embodiment shown, the single use imaging device 120 also includes a breakout box 126 that is positioned approximately midway along the length of the endoscope. The breakout box 126 provides an entrance to a working channel and may include additional attachment points for collection of samples and surgical manipulation. The control unit 200 includes a device interface 210 and a network interface 220. The device interface 210 allows the single use imaging device 120 to transfer a stored code in the format of an image signal to the control unit for analysis. While the illustrative embodiment of the system depicted in FIG. 1 shows an endoscope as the imaging device, it will be understood by one skilled in the art that any type of single use imaging device can be used in accordance with the devices, systems and methods of the invention.

Figure 2:
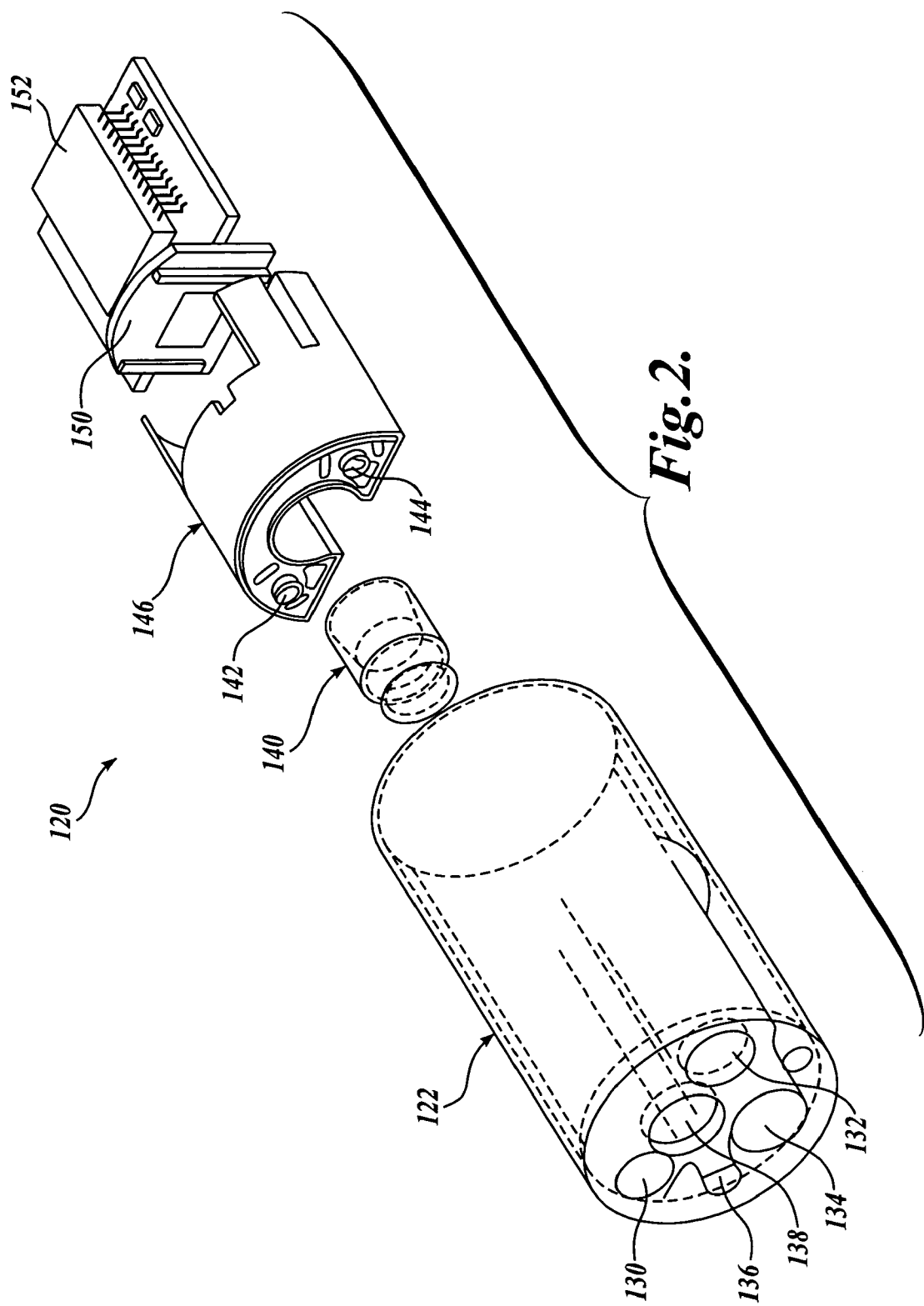
FIG. 2 is a schematic diagram of an imaging system of a single use imaging device in accordance with an embodiment of the present invention.

FIG. 2 shows further detail of one embodiment of an imaging sensor assembly positioned at or adjacent to the distal tip 122 of an exemplary single use imaging device 120. The distal tip 122 includes light illumination ports 130 and 132, an entrance to a working channel 134, a camera port 138 and a flushing cap 136. With continued reference to FIG. 2, the imaging assembly includes a cylindrical lens assembly 140, and a pair of LEDs 142 and 144 bonded to a circuit board 152 which is affixed to a heat exchanger 146. Fitted to the rear of the heat exchanger 146 is an image sensor 150 that preferably comprises a CMOS imaging sensor chip or other solid state imaging device. A circuit board or flex circuit 152 is secured behind the image sensor 150 and contains circuitry to transmit and receive signals to and from the control unit 200. The image sensor 150 is preferably a low light sensitive, low noise, CMOS color imager with VGA resolution or higher such as SVGA, SXGA, or XGA. If less resolution is required, a one-half VGA sensor could also be used. The video output of the system may be in any conventional digital or analog format, including PAL or NTSC or high definition video format. In some embodiments, the image sensor 150 comprises a VGA CMOS image sensor with 640×480 active pixels and an on-chip serializer that transmits image data to the control cabinet in a serial form. Such a CMOS image sensor is available as Model No. MI-370 from Micron Electronics of Boise, Id. Further detail of the imaging system and its generation can be found in U.S. Pat. No. 10/811,781 filed Mar. 29, 2004 and which is herein incorporated by reference.

In some embodiments of the present invention, the single use imaging device 120 comprises a memory having a code stored therein that encodes a serial identifier uniquely associated with the imaging device. The code is transferable to the control unit in the same format as image signals are transmitted to the control unit 200 for analysis. The memory may be provided in the circuit board 152 and coupled to the image sensor 150, or the memory may be integrated within the image sensor 150. Alternatively memory chips may also be added at, or adjacent to, the proximal end 122 of the imaging device 120. The memory can be any digital memory which is designed to store individual bits of information. Code information such as a program or data can be programmed into a memory chip at the time of manufacture. Code information encoding a unique serial identifier or a verification object image embedding a code can be programmed or "burned" into the chip at the time of manufacture. The serial identifier is in general a character string of sufficient length to uniquely characterize a single unit from within large production runs. The identifier could be similar to the codes used in familiar UPC barcodes (see, e.g., the Uniform Code Council, Inc., Princeton Pike Corporate Center, 1009 Lenox Drive, Suite 202, Lawrenceville, N.J. 08648) or more extensive codes such as web addresses (uniform resource locators, URLs). The character string can be impressed upon an EPROM component included in the single use-device camera electronics or stored at manufacture in nonvolatile memory. In a preferred embodiment of the invention, the image sensor 150 stores in its memory an image signal that contains the serial identifier used to authorize the single use device in the same format as the medical images obtained during clinical use of the device.

In accordance with this aspect of the invention, the imaging device 120 is capable of transferring the code containing a serial identifier in the format of the image signals produced by the image sensor to the control unit 200 for analysis. In order to transmit serial image data and control signals along the length of the endoscope, the data and control signals are preferably sent differentially along a pair of twisted micro-coaxial cables. The stored code encoding the serial identifier can be read as a video output signal by the control unit and used to determine if use of the imaging device is authorized.

In another aspect, the present invention provides a control unit 200 for authorizing a single use imaging device comprising an interface that is capable of receiving an electronic image that includes a unique serial identifier. The code may be stored in the memory of a single use imaging device as described above, or, alternatively, the code may be embedded in a verification object image that is obtained from a test target associated with the single use imaging device as further described below.

Figure 3:
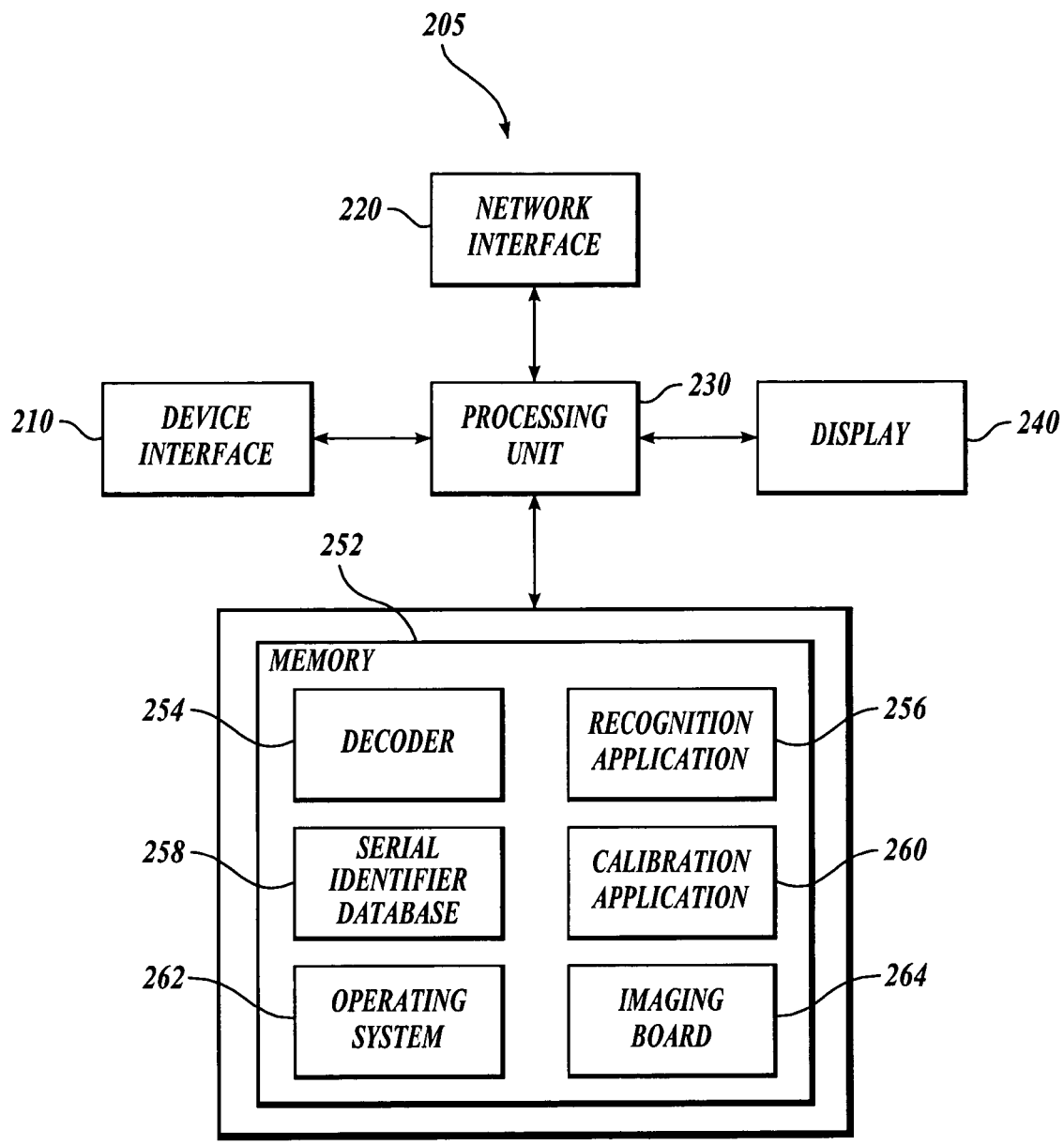
FIG. 3 is a block diagram of an illustrative architecture for a control unit for a single use imaging device in accordance with the present invention.

FIG. 3 is a block diagram of an illustrative architecture for a control unit 200 containing a computer 205 in accordance with this aspect of the invention. Those of ordinary skill in the art will appreciate that the computer 205 may include additional components. However, it is not necessary that all of these generally conventional components be shown in order to disclose an illustrative embodiment of the invention. As shown in FIG. 3, the exemplary embodiment of the control unit 200 shown includes a network interface 220, a processing unit 230, a device interface 210, a display 240 and an image processor 242 that are connected to the processing unit 230. The computer 205 also includes a memory 252 that stores a serial identifier database 258, an image recognition program 256, a calibration program 260, and an operating system 262. The memory 252, display 240, network interface 220, and device interface 210 are all connected to the processor 230 via a bus. Other peripherals may also be connected to the processor in a similar manner. Although the embodiment of the computer 205 shown in FIG. 3 contains a calibration program 260 and a local database 258, these features are optional and not required in some embodiments of the invention. In some embodiments of the invention, the calibration program 260 interfaces with a servo motor controller (not shown) that in turn controls a number of servo motors. Each of the servo motors is connected to one or more control cables within the endoscope. Motion of the servo motors pulls or releases the control cables in order to change the orientation of the distal tip 122 of the imaging device 120.

Those of ordinary skill in the art will appreciate that the network interface 220 includes the necessary circuitry for connecting the computer 205 directly to a LAN or WAN, or for connecting remotely to a LAN or WAN with various communication protocols, such as the TCP/IP protocol, the Internet Inter-ORB protocol, any of various wireless protocols (e.g., the IEEE 802.1x family) and the like. The device interface 210 includes hardware and software components that facilitate interaction with a device that provides an input digital image, such as an electronic image sensor (FIG. 2). The interface can receive an input digital signal via a wired connection, or alternatively, via a wireless signal from the single use imaging device. The processing unit 230 is of sufficient power and speed to provide processing of an input digital image either alone or in cooperation with the image processor 242.

With continued reference to FIG. 3, the memory 252 generally comprises a random access memory ("RAM"), a read-only memory ("ROM") and a permanent mass storage device, such as a hard disk drive, tape driver, optical drive, floppy drive, CD-ROM, DVD-ROM or removable storage drive. The memory 252 stores an operating system 262 for controlling operation of the computer 205.

In operation of one embodiment of the authorization system 100, upon attachment of the imaging device 120 to the control unit 200, the imaging element in the distal tip 122 of the device 120 becomes activated and captures an image of the verification object 400 that is printed on the test target 410 (FIG. 1). In another embodiment of the authorization system 100, the image of verification object 400 is pre-stored in the memory of the single use device (FIG. 2) as a code at the time of manufacture. The image of verification object 400 is transferred from the endoscope imaging element (or other memory) to the control unit 200. The computer 205 and the image processor 242 receives the image of the verification object and extracts the serial identifier of the single use imaging device. To decode the serial number, the processor 230 and/or the image processor executes an image decoder program that detects digitized bar space patterns or other predetermined spatial, color or numeric codes to detect the serial number.

Once the image of the verification object 400 has been decoded into the serial identifier, the authorization system 100 authorizes the device for use by comparing the serial identifier to a database of authorized serial identifiers. In some embodiments, as shown in FIG. 3, the serial identifier database 258 is stored locally in the memory 252 of the computer 205 contained within the control unit 200, and the determination is made using the recognition program 256. The database 258 may be downloaded from a remote location such as from the manufacturer of the single use imaging device into the memory of the computer 205 via a local area network. Alternatively, periodic updates to the serial identifier database 258 may also be provided on a CD-ROM or other machine-readable storage medium and accessible via the network interface 220 or by using a CD-ROM drive within the control unit 200 itself. The serial number database may also include additional information such as model information, product recall notices, product parameter updates, and the like.

Figure 4:
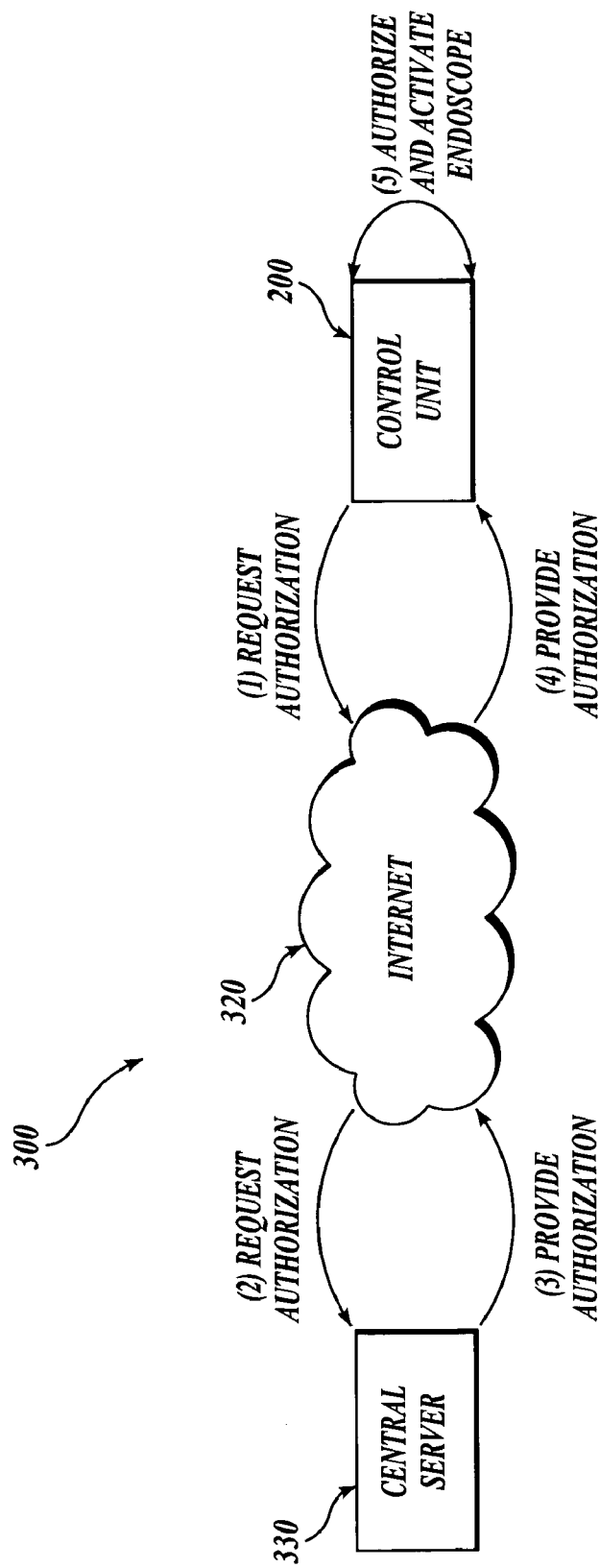
FIG. 4 illustrates the transfer of authorization data between a control unit and a remote central server in accordance with one embodiment of the present invention.

In another embodiment of the invention, the serial number database 258 is located at a remote central server that registers the use of single use imaging devices and marks a particular device as having been used to prevent future authorization. FIG. 4 illustrates the operation of a remote authorization system 300 to transfer authorization information regarding a particular serial identifier between the control unit 200 connected to the single use imaging device 120 and a remote central server 330 accessible via the Internet 320. In operation, a user may be positioned in front of a display device 240 connected to the control unit 200 and may initiate a request for authorization of a single use imaging device based upon the serial identifier decoded from the verification object. Alternatively, a request for authorization may be automatically initiated by the control unit 200 via the network interface 220 (FIG. 1). As shown in FIG. 4, two-way communication may be initiated by accessing the central server 330 from the control unit 200. Once a connection has been established, the control unit 200 may configure the transmission of a request for authorization for a particular serial identifier, as shown in the embodiment of system 300 depicted in FIG. 4. The central server 330 receives the serial identifier and sends an appropriate response as to whether the device is authorized to the control unit 200 via the Internet 320. In some embodiments of the authorization system 300, the remote central server comprises a registry that tracks usage information of single use medical devices.

Figure 5A:
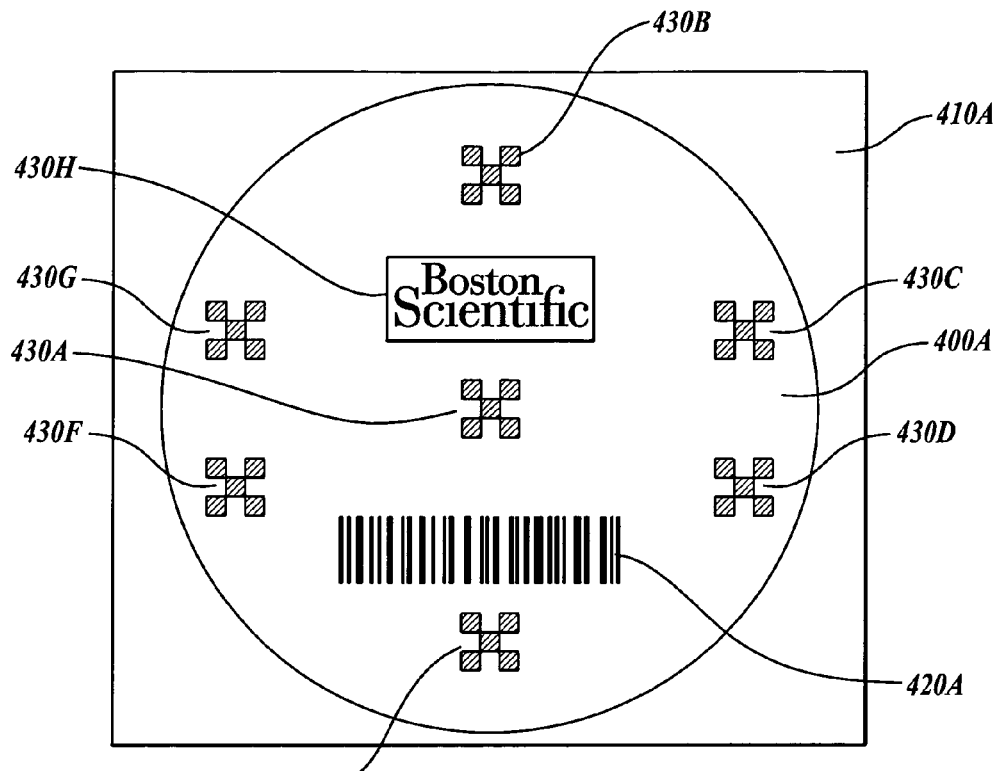
FIG. 5A illustrates an embodiment of a verification object image that encodes a serial identifier in the form of a linear bar code and a set of calibration objects.
Figure 5B:
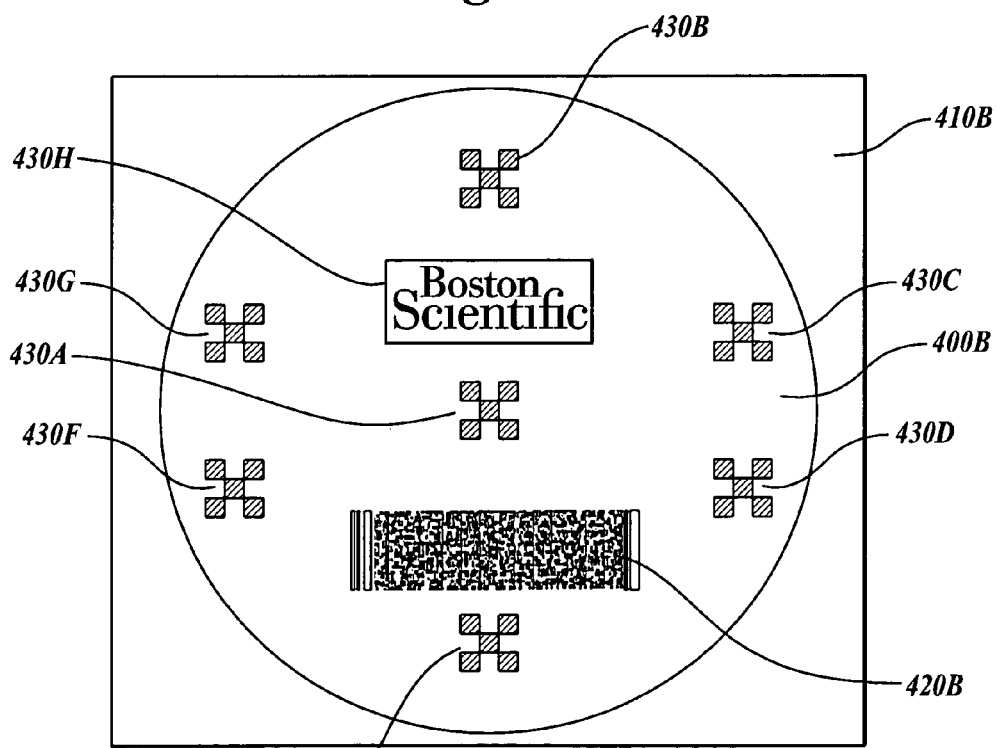
FIG. 5B illustrates an embodiment of a verification object image that encodes a serial identifier in the form of a two-dimensional bar code and a set of calibration objects.

In some embodiments of the authorization system 100, as shown in FIG. 1, the verification object image 400 is printed onto a test target 410 that is associated with the imaging device 120 at the time of its manufacture. The serial identifier encoded in the verification object image can be any combination of letters, symbols, characters, colors or patterns capable of uniquely identifying a single use imaging device. A serial identifier can be encoded in any type of machine readable image, such as a linear bar code or a two-dimensional bar code as further described below. FIGS. 5A and 5B illustrate a verification object image 400A,B printed on a test target 410A,B. The verification object image 400A,B includes an encoded serial identifier 420A,B that is uniquely associated with a single use device at time of its manufacture. In the exemplary embodiments shown in FIGS. 5A and 5B, the verification object images 400A,B additionally include a set of imaging calibration objects 430A-H.

In some embodiments, such as that shown in FIG. 5A, the serial identifier is encoded in a linear bar code 420A. As shown, the exemplary linear bar code 420A illustrated in FIG. 5A is a series of vertical lines of varying widths (called bars) and spaces. Different combinations of the bars and spaces represent different characters. To decode the serial number, the processor 230 or image processor executes a bar code reading program that detects the patterns of bars and spaces in the image of the verification object. For example, the linear bar code 420A may represent numeric characters only (e.g., UPC, EAN, Interleaved 2 of 5), or may represent both numbers and alphabetic characters (e.g., Code 93, Code 128 and Code 39).

In other embodiments, such as that shown in FIG. 5B, the serial identifier is encoded in a two-dimensional bar code 420B. As illustrated in FIG. 5B, the two-dimensional bar code 420B stores information along the height as well as the length of the symbol. Illustrative non-limiting examples of two-dimensional bar codes useful in the present invention include stacked bar codes, PDF417 codes, and data matrix codes.

In a preferred embodiment, the serial identifier 420A,B of the single use device 120 will comply with the voluntary labeling standards developed by the Health Industry Business Communications Council (HIBCC). The HIBCC labeler identification code (LIC) primary data structure specifies the use of either Code 128 or Code 39 symbology which utilize an alphanumeric character set. The 36 alpha and numeric characters combined with the flexibility of a 1-13 digit variable length format provide over 75 million trillion identifiers, thereby vastly reducing the possibility of duplicate identifiers in the same database. HIBCC standards further specify the use of two-dimensional symbologies, such as data matrix and PDF417 for small device and instrument marking (see "The Health Industry Bar Code Supplier Labeling Standard," American National Standards Institute, Inc. (ANSI), Health Industry Business Communications Council, 2525 East Arizona Biltmore Circle, Suite 127, Phoenix, Ariz. 85016, incorporated herein by reference).

In further embodiments, the verification objects 400A,B that are printed on the test targets 410A,B include a set of calibration objects. FIGS. 5A and 5B illustrate an exemplary set of calibration objects 430A-H useful for calibrating the imaging element of the single use imaging device 120. Each calibration object 430A-H is positioned at predetermined point coordinates within the verification object image. The positioning of the calibration objects 430A-H allows an imaging device to capture the verification object image 400A,B, and to determine if the position of the calibration objects is distorted in comparison to a pre-set standard with respect to focus, radial distortion, warping, and the like. The calibration objects 430A-H may also be positioned on various surfaces in order to test the motor and steering function of the image device 120. The pre-set standard may be stored as code within the single use device and transmitted to the imaging board in the format of an imaging signal as previously described. Alternatively, the pre-set standard may be stored locally in the control unit or obtained via a network connection upon authorization.

The image of verification object 400A,B may be captured from the test target 410A,B using the imaging device 120 at various deflection angles or focal lengths/zoom settings (if available). In operation, the calibration objects 430A-H are compared to the pre-set standards using the calibration program 260. Once a distortion or other discrepancy is detected, a set of coefficients is derived and used to perform a corrective calibration, if necessary, prior to clinical use of the device. In some embodiments, the verification object 400A,B contains at least four calibration objects. In some embodiments, the verification object image 400A,B contains at least seven calibration objects 430A-H. In some embodiments, the identical calibration object is positioned at two or more different predetermined locations within the verification object as shown in FIGS. 5A,B calibration objects 430A-H. In some embodiments, two or more calibration objects within a particular verification object image are different from one another (see FIGS. 5A,B calibration objects 430A and 430H). In some embodiments, a principal calibration object may be designated in the center of the image. In addition, an orientation calibration object may also be designated. In addition to predetermined positions of the calibration objects, the pixel aspect ratio of the imaging element can be calibrated based on detection of the pixel value of the calibration objects in order to adjust contrast, white-balance and exposure control of the imaging device. In some embodiments, a set of calibration objects are provided without a serial identifier.

The test target 410A,B can be any item upon which the verification object 400A,B associated with the device 120 can be printed and that is accessible to the imaging element in the distal tip 122. For example, test target 410A,B may be printed on packaging associated with the device 120 or on an accessory such as a cap, cable, or other accessory. In some embodiments, the test target 410A,B is imprinted directly onto the device 120 at a position where the image sensor can be positioned to capture an image of the verification object.

In some embodiments, the test target 410A,B is provided on a three dimensional structure, such that the calibration objects 430A-H are positioned at various deflection angles with respect to the position of the distal tip 122 of the imaging device 120. For example, a set of calibration objects could include targets at the corners of the specified deflection range, which would be imaged in sequence to verify that the navigation function is working correctly and the device can be steered, e.g., to its up/down/left/right limits. These calibration objects could include encoded identifiers of their location, so that the response to simulated user commands regarding position and transit time can be measured, compared to quality assurance criteria, passed with respect to acceptability thresholds (which can be tailored to individual users and procedures) and reported to a central database.

The three dimensional positioning of the calibration objects 430A-H provides objects with which to test the steering and motor functions of the single use imaging device 120. For example, the test target 410A,B may be printed on various surfaces of a hood that is placed over the distal tip 122. As another example, the test target 410A,B may be printed on several panels of packaging material provided with the device. The packaging material may be folded into various shapes, such as a box shape to allow for image capture at various deflection angles. In such embodiments, the test targets 410A,B are positioned at an appropriate distance for the focal properties of the imaging device 120.

There are various methods of printing the verification object 400 on the test target 410 in accordance with some embodiments of this aspect of the invention. In some embodiments, the printed verification object image contains an encoded serial identifier uniquely associated with a particular single use device. In other embodiments, the printed verification object image contains both an encoded unique serial identifier and a set of calibration objects. In such embodiments, the set of calibration objects are identical for a particular set of devices, such as a particular model of device, while the serial identifiers are different for each device. The verification object 400A,B can be printed on the test target 410A,B using labeling software with a printer (dot matrix, laser or inkjet printer) and affixing the image to the test target 410A,B, or by printing the verification object image 400A,B with a specialized bar code label printer. In some embodiments, verification object images in the form of data matrix can be etched directly onto a single use device 120.

Figure 6:
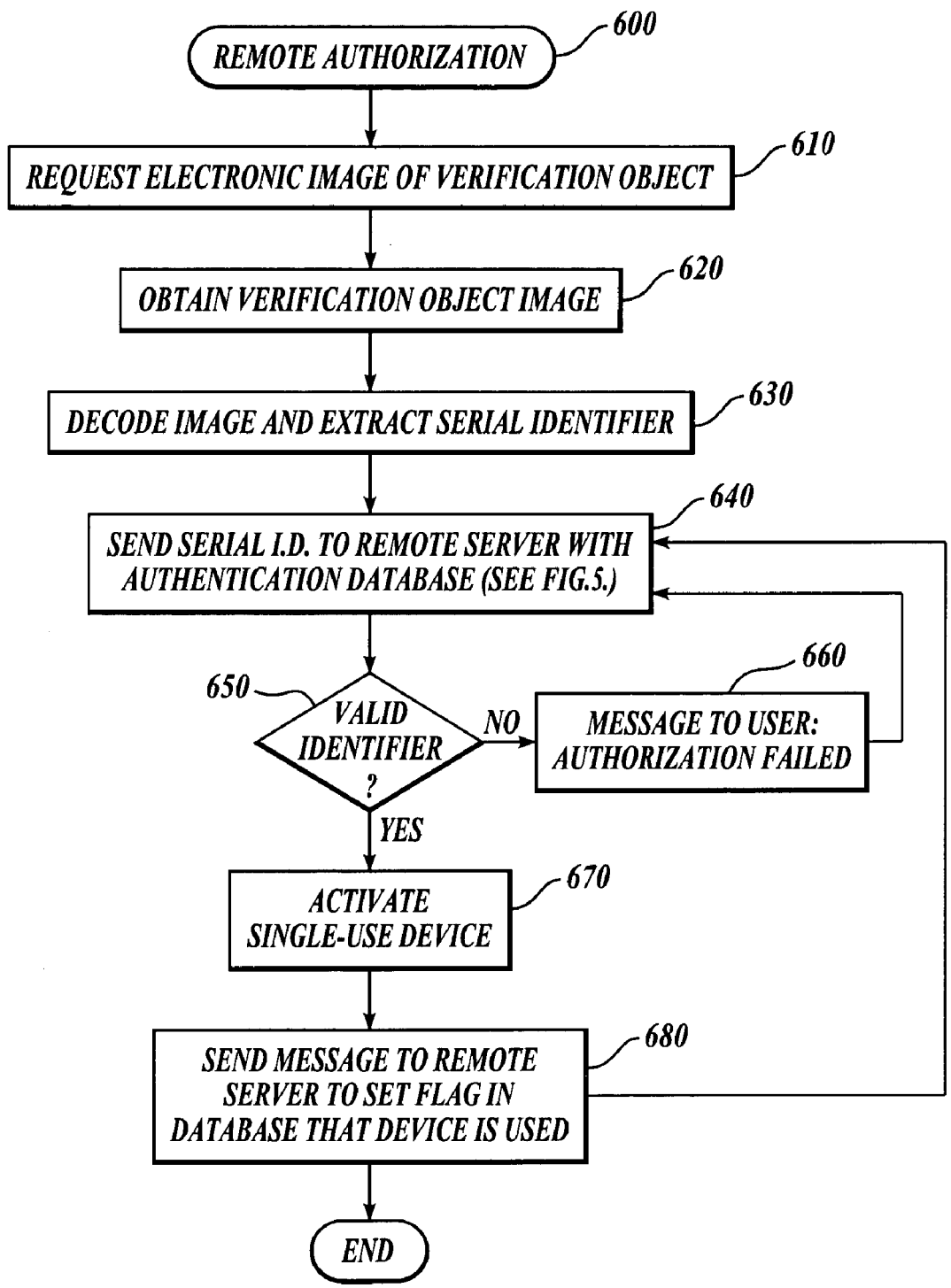
FIG. 6 is a flow diagram of a process for remotely authorizing use of a single use medical device according to another embodiment of the method of the invention.

In another aspect, the present invention provides methods for authorizing a single use imaging device. In some embodiments of this aspect of the method of the invention, authorization is verified remotely. FIG. 6 is a flow chart of a process for remote authorization using a verification object. The remote authorization process begins at 600 and comprises requesting an electronic image of the verification object associated with the single use device at 610, and obtaining the verification object image at 620. As indicated above, the control unit requests the verification image after the single use device is connected to the control unit. In some embodiments, the electronic image is obtained from the memory of the single use device. In other embodiments, the electronic image is obtained using the imaging sensor of the single use device. Once the machine obtains the electronic image, the image is decoded to extract the serial identifier at 630. The machine then sends the serial identifier information to a remote server with an authentication database at 640. A test is made at 650 to determine if the serial identifier is valid. If not, the remote server sends a message to the user that the device is not authorized at 660, and there is no activation. If the remote server verifies that the serial identifier is authorized, a message is sent that the identifier is valid at 650 and activation of the device is allowed at 670. The activation of the device triggers a message to the remote server to flag the database or otherwise indicate that the device has been used at 680.

The use of the remote authorization method of the invention allows a service provider of a central server, such as a manufacturer of a device, to maintain a registry of new authorized devices associated with unique serial identifiers and to prevent unauthorized use or reuse of a device. Once a device is registered as used, the serial identifier is flagged or otherwise marked as having been used so that the identical identifier will not be authorized for future use. Using a real-time server logic, the authorization information can be returned to the client. There are various suitable methods for providing user registration and tracking of single use imaging devices, including, for example, sending the serial identifier to a Web server application with an automatic real-time response. Upon request for verification from a user, the service provider can determine that the device is new, and also provide important upgrades prior to unlocking features required for activation, thus maintaining control over single use devices.

Moreover, the use of the remote authorization method allows a central server to verify that the client is a licensed customer, by receiving an identification number associated with the client when the request for authorization is made. For example, the central server may require information in addition to the serial identifier such as the control unit serial number, the client's name and location, and the like before the device is authorized for use.

Figure 7:
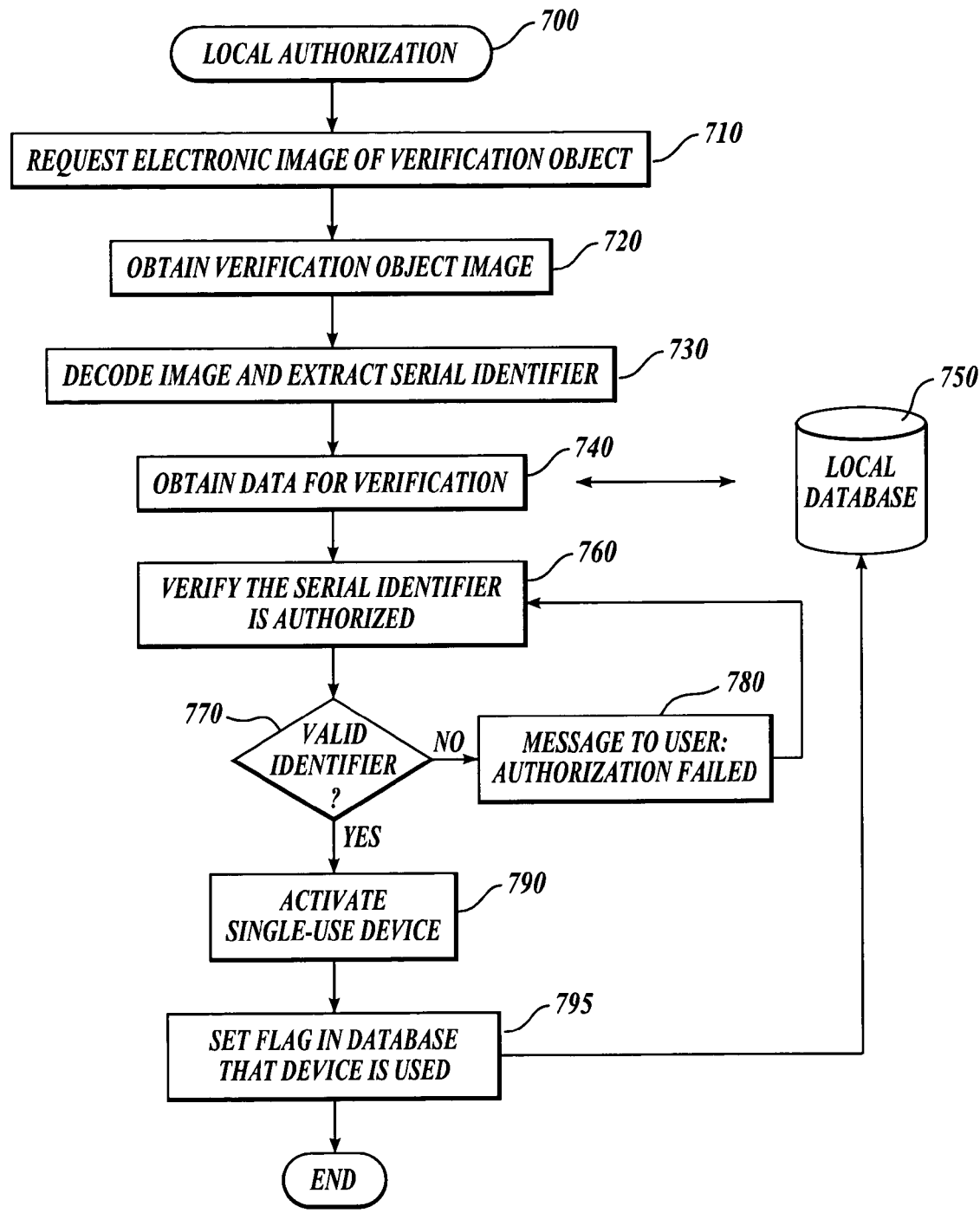
FIG. 7 is a flow diagram of a process for locally authorizing use of a single use medical device according to another embodiment of the method of the invention.

Alternatively, in another embodiment, the invention provides a method for local authorization. FIG. 7 is a flow diagram of a process for local authorization and activation using a verification object. The local authorization process starts at 700 and comprises requesting an electronic image of the verification object associated with the single use device at 710, and obtaining the verification object image 720. Once the control unit obtains the electronic image, the image is decoded to extract the serial identifier at 730. The control unit then obtains data for a verification at 740 from a local database at 750. The control unit then verifies that the serial identifier is authorized at 760 by comparing the serial identifier to information in the database using a set of predetermined rules for authorization.

In some embodiments, the local database contains a list of authorized serial identifiers provided by the manufacturer of the single use device which may be entered into the control unit via a CD-ROM, or other form of electronic download such as a periodic Internet update. Such authorization data may include the serial identifiers, as well as other information for updating the rules for authorization. Thus, the authorization rules and serial identifiers may be dynamically updated so that a control unit receives and maintains authorization rules and data that are current. A test is made to determine if the serial identifier is valid at 770. If not, the control unit provides a message to the user at 780 that the device is not authorized, and there is no activation. If the serial identifier is determined to be valid at 770, the single use device is authorized and activated at 790. Upon activation, the control unit sends a message to the database at 750 to set a flag or otherwise indicate that the device has been used at 795. This indication in the database allows a user to track the usage of the single use device and to verify that any imaging device connected to the control unit is new and unused.

Figure 8:
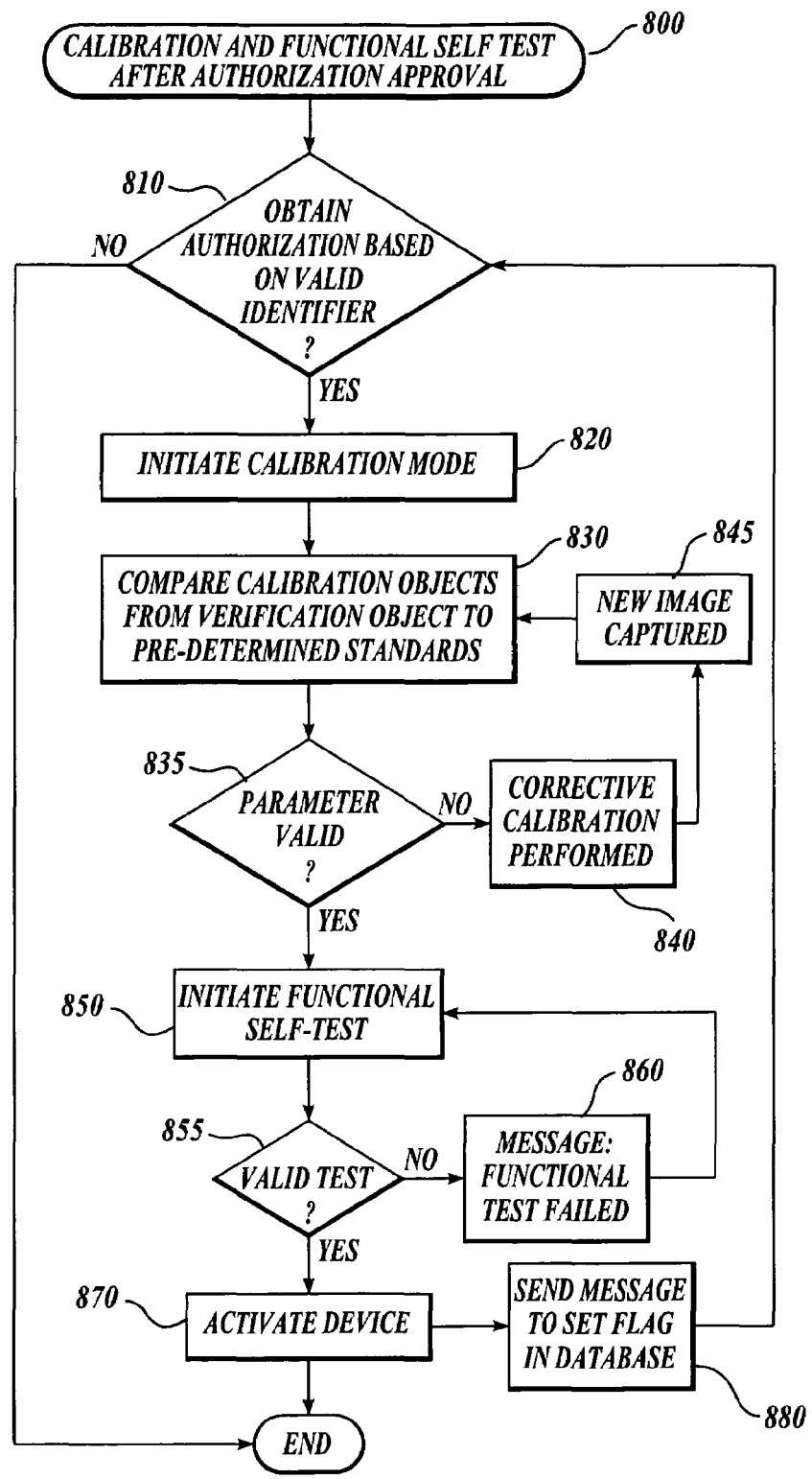
FIG. 8 is a flow diagram of a process for authorization, calibration and self-testing in accordance with another embodiment of the present invention.

In some embodiments, the features used for authorization further allow the calibration and functional self-testing of the single use imaging device. As shown in FIG. 8, a calibration and self-test process begins at 800 and comprises obtaining authorization based on a valid identifier at 810 and initiating a calibration mode at 820. In the calibration mode, calibration objects obtained from the verification object image are compared to pre-set standards at 830. A test is made at 835 to determine if the calibration parameters are valid. If not, a corrective calibration is performed at 840, a new image of the verification object is captured at 845, and the calibration objects from the most recent verification object image are compared to the pre-set standards at 830. If the parameters at 835 are determined to be valid, the control unit initiates a functional self-test at 850. In some embodiments, the self-test parameters are updated during the authorization process. Self-test parameters may include navigation functions such as motor functions, steering and braking functions, transient response, position accuracy or error, and imaging functions like color fidelity, balance, sensitivity, linearity across a field, glare, blooming, etc. If the device fails the functional self-test at 850, a message is returned to the user that the functional test failed at 860. If the device passes the functional self-test, the single use device is activated for use at 870. Upon activation, a message is sent to the database to set a flag or otherwise indicate that the device is used at 880. A corrective calibration and functional testing may be automatically performed by the control unit using predetermined algorithms, or alternatively, these functions may be performed by the user utilizing user-interactive commands.

Figure 9:
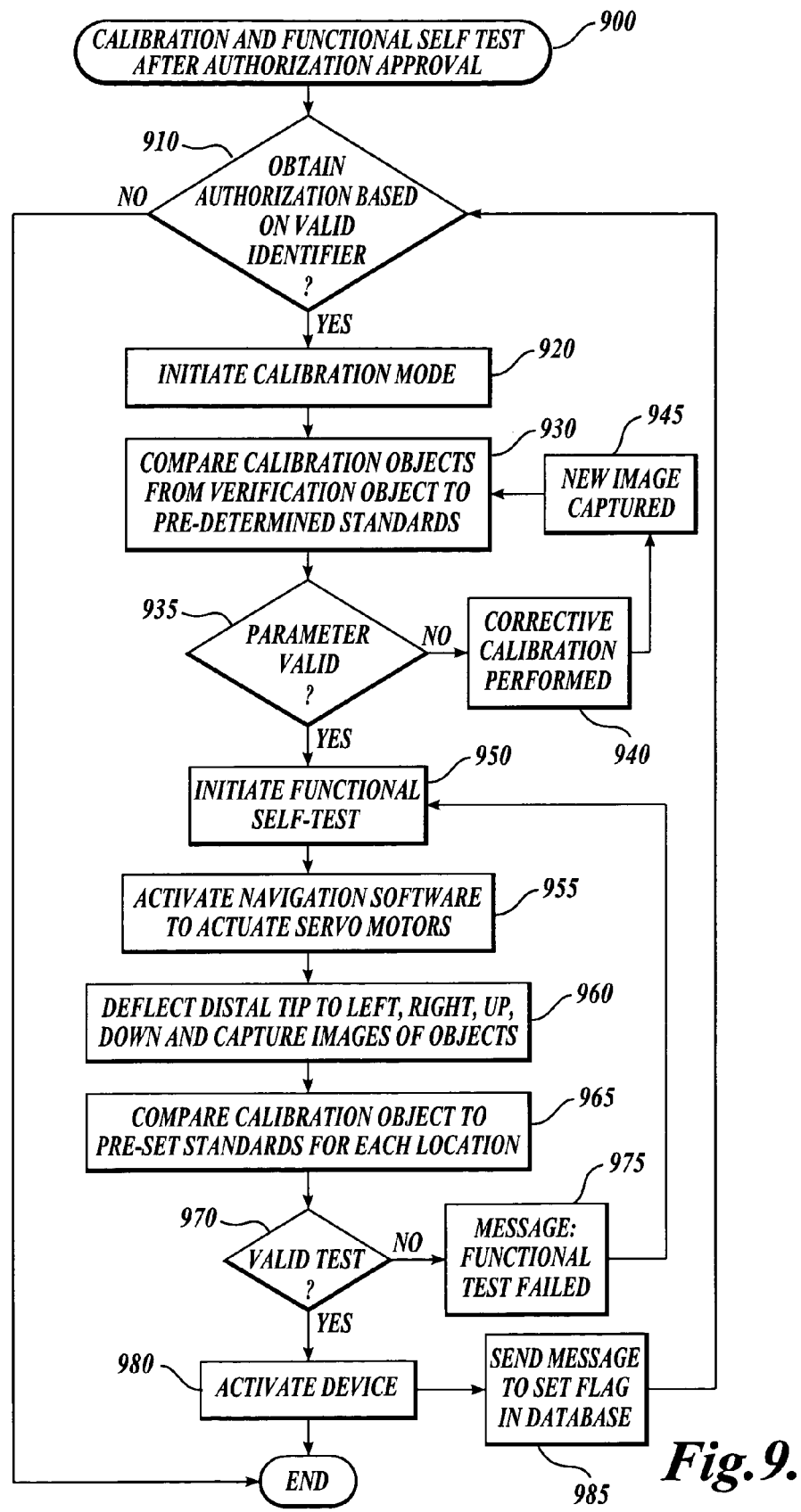
FIG. 9 is a flow diagram of a process for authorization, calibration and self-testing in accordance with yet another embodiment of the present invention.

In some embodiments, the features used for calibration allow for functional self-testing of the single use imaging device. As shown in FIG. 9, a calibration and functional self-test process begins at 900 and comprises obtaining authorization based on a valid identifier at 910 and initiating a calibration mode at 920. In the calibration mode, calibration objects obtained from the verification object image are compared to pre-set standards at 930. A test is made at 935 to determine if the calibration parameters are valid. If not, a corrective calibration is performed at 940, a new image of the verification object is captured at 945, and the calibration objects from the most recent verification object image are compared to the pre-set standards at 930. If the parameters at 935 are determined to be valid, the control unit initiates a functional self-test at 950. In the functional self-test mode, a navigation program is activated that actuates servo motors connected to cables inside the single use imaging device at 955. The distal tip of the imaging device is deflected at various angles (left, right, up, down, and the like) in order to aim at and capture an image of each calibration object at 960. Once an image of each calibration object is captured, the image is compared to pre-set standards for each location at 965. A test is made at 970 to determine if the device functional parameters are valid. The functional parameters may include motor functions, steering and capture of images at predetermined locations. If the device fails the functional self-test at 970, a message is returned to the use that the functional test failed at 975. If the device passes the functional self-test, the single use device is activated for use at 980. Upon activation, a message is sent to the database to set a flag or otherwise indicate that the device is used at 985. Those of ordinary skill in the art will recognize that the calibration and functional self-testing functions may be accomplished in a variety of sequential steps. For example, a functional self-test may be performed prior to or concurrent with the steps of calibration.

Although the presently preferred embodiment of the invention serializes a single use endoscope, those skilled in the art will recognize that the invention is applicable to other single use medical imaging devices such as catheters, imaging guide wires and the like. The methods of this aspect of the invention comprise assigning a unique serial identifier to each single use imaging device to be manufactured, encoding the serial identifier in a verification object image, and associating the serial identifier with the device at the time of manufacture. The verification object image may also include a set of calibration objects, thereby allowing a device to be authorized and calibrated using the same captured validation object image. The method further includes maintaining a database of authorized serial identifiers corresponding to manufactured serialized medical devices to users. In accordance with this aspect of the invention, the user of the medical device may determine if a particular device is authorized by comparing the unique serial identifier to the database of manufactured serialized medical devices by utilizing the systems and methods of the invention previously described. The method of calibration using a captured validation object may be performed as described herein.

While the preferred embodiment of the invention has been illustrated and described, it will be appreciated that various changes can be made therein without departing from the scope of the invention. It is therefore intended that the scope of the invention be determined from the following claims and equivalents thereof.

The invention claimed is:

1. A single use medical imaging device that is removably connected to a control unit, comprising:
   a shaft having a proximal end and a distal end,
   a connector on the proximal end for connecting the device to a control unit;
   an image sensor at or adjacent to the distal end of the device for producing images in a predefined format for receipt by an imaging board within the control unit;
   a memory having a code stored therein that encodes a serial identifier uniquely associated with the imaging device; and
   a transmit circuit that transmits the code to the imaging board in the format of the image signals produced by the image sensor.

2. The imaging device of claim 1 wherein the memory is coupled to the image sensor.

3. The imaging device of claim 1 wherein the memory is integrated within the image sensor.

4. The imaging device of claim 1 wherein the code is embedded in an image of a verification object that is stored within the memory.

5. The imaging device of claim 4 wherein the image of the verification object includes an image of a linear bar code.

6. The imaging device of claim 4 wherein the image of the verification object includes an image of a two-dimensional bar code.

7. The imaging device of claim 4 wherein the verification object image further includes a set of calibration objects.

8. A control unit for authorizing a single use medical imaging device comprising:
   a connector for connecting the control unit to the single use medical imaging device;
   a device interface capable of receiving a code in a format of an image signal produced by the image sensor within the medical imaging device, wherein the code encodes a serial identifier uniquely associated with the imaging device;
   a processor that decodes the serial identifier from the image signal; and
   means for determining if the single use imaging device is authorized based upon the serial identifier associated with the device.

9. The control unit of claim 8, wherein the code is embedded in an image of a verification object.

10. The control unit of claim 8, wherein the verification object further comprises one or more patterns to calibrate the single use imaging device.

11. The control unit of claim 8, wherein the verification object further comprises one or more patterns to functionally test the single use imaging device.

12. A medical imaging system comprising:
    a single use medical imaging device, having a shaft with a proximal end and a distal end;
    a connector on the proximal end for connecting the device to a control unit;
    an image sensor at or adjacent to the distal end for producing images in a predefined format for receipt by an imaging board within the control unit;
    an image of a verification object encoding a serial identifier uniquely associated with the device;
    a transmit circuit that transmits the image of the verification object to a control unit in the predefined format of the image signals produced by the image sensor;
    a control unit for authorizing a single use medical imaging device including:
    a connector for connecting the control unit to a single use medical imaging device;
    a device interface capable of receiving an image of the verification object in the predefined format of an image signal produced by the image sensor of the medical imaging device;
    a processor that determines if the single use imaging device is authorized based upon the serial identifier associated with the device.

13. The system of claim 12, wherein the image of the verification object image is stored in the memory of the single use device.

14. The system of claim 12, wherein the verification object is printed on a test target uniquely associated with the single use device at the time of manufacture.

15. The system of claim 12, wherein the means for determining if the imaging device is authorized compares the serial identifier to a registry contained in a remote database accessible from the control unit to determine if the device associated with the unique identifier has ever been used before.

16. The medical imaging system of claim 12 wherein the verification object image includes a linear bar code.

17. The medical imaging system of claim 12 wherein the verification object image includes a two-dimensional bar code.

18. The medical imaging system of claim 12 wherein the verification object image further includes a set of calibration objects.

19. The medical imaging system of claim 18 wherein the calibration objects are printed on a test target at various deflection angles.

20. A method for authorizing a single use imaging device comprising:
    connecting the single use imaging device to a control unit;

electronically obtaining an image of a prerecorded verification object associated with the imaging device wherein the verification object image encodes a serial identifier;

extracting the serial identifier from the image of the verification object; and authorizing the use of the imaging device by comparing the serial identifier to a database containing information on authorized serial identifiers, wherein a match between the serial identifier and information in the database results in authorization for use.

21. The method of claim 20 wherein the image of the prerecorded verification object is obtained using the electronic imaging element of the imaging device.

22. The method of claim 20 wherein the prerecorded verification object is printed on a test target uniquely associated with the device at the time of manufacture.

23. The method of claim 20 wherein the database is a registry at a remote central server.

24. The method of claim 20 wherein the verification object encodes a unique serial identifier and a set of calibration objects.

25. The method of claim 24 wherein the calibration objects are printed on a test target at various deflection angles.

26. A method of automatically authorizing and self-testing a medical device containing an image element comprising the steps of:

recognizing the medical device as authorized based upon electronic detection of an image of a prerecorded verification object;

automatically calibrating the device using calibrating features included in the verification object;

functionally testing the device; and activating the device upon successful authorization, calibration and functional testing.

27. The method of claim 26, wherein a registry records the results of the calibration and functional testing of the medical device.

* * * * *